(12) United States Patent　　(10) Patent No.:　　US 7,548,784 B2
Chinchoy　　(45) Date of Patent:　　*Jun. 16, 2009

(54) METHOD AND APPARATUS FOR OPTIMIZING CARDIAC RESYNCHRONIZATION THERAPY

(75) Inventor: Edward Chinchoy, Golden Valley, MN (US)

(73) Assignee: Medtronic, Inc., Minneapolis, MN (US)

( * ) Notice: Subject to any disclaimer, the term of this patent is extended or adjusted under 35 U.S.C. 154(b) by 541 days.

This patent is subject to a terminal disclaimer.

(21) Appl. No.: 11/085,844

(22) Filed: Mar. 22, 2005

(65) Prior Publication Data

US 2005/0165454 A1　　Jul. 28, 2005

Related U.S. Application Data

(63) Continuation of application No. 10/394,777, filed on Mar. 20, 2003, now Pat. No. 6,871,088.

(51) Int. Cl.
*A61N 1/00*　　(2006.01)

(52) U.S. Cl. .................................................. 607/17

(58) Field of Classification Search ................ 607/6, 607/17, 23; 600/485, 486, 490, 500, 503, 600/508, 509, 510, 519, 526
See application file for complete search history.

(56) References Cited

U.S. PATENT DOCUMENTS 5,480,412 A * 1/1996 Mouchawar et al. ........... 607/6
5,626,623 A * 5/1997 Kieval et al. .................. 607/23
5,978,710 A * 11/1999 Prutchi et al. ................. 607/17

* cited by examiner

*Primary Examiner*—George Manuel
(74) *Attorney, Agent, or Firm*—Stephen W. Bauer

(57) ABSTRACT

A method and apparatus for optimizing cardiac resynchronization therapy are provided. An iterative optimization procedure is performed to test the systolic hemodynamic effects of varying A-V-V timing schemes. The hemodynamic effect is assessed based on a surrogate of stroke volume. The stroke volume surrogate is derived from a sensor signal proportional to the blood pressure in the aorta or a major artery. The A-V-V timing scheme corresponding to the highest magnitude stroke volume, as indicated by the stroke volume surrogate, is identified and automatically programmed to maintain optimal A-V-V settings acutely and chronically.

19 Claims, 6 Drawing Sheets

METHOD AND APPARATUS FOR OPTIMIZING CARDIAC RESYNCHRONIZATION THERAPY

CROSS REFERENCE TO RELATED APPLICATION

The present patent document is a continuation of prior, co-pending non-provisional patent application Ser. No. 10/394,777, which issued as U.S. Pat. No. 6,871,088 to Edward Chinchoy on 22 Mar. 2005, the contents of which are hereby incorporated herein by reference.

FIELD OF THE INVENTION

The present invention relates generally to medical devices for treating cardiac dysfunction and more particularly to a device and method for optimizing cardiac resynchronization therapy acutely and/or chronically based on a hemodynamic surrogate measurement for stroke volume.

BACKGROUND OF THE INVENTION

Evaluation of left ventricular function is of interest for both diagnostic and therapeutic applications. During normal cardiac function the cardiac chambers observe consistent time-dependent relationships during the systolic (contractile) phase and the diastolic (relaxation) phase of the cardiac cycle. During cardiac dysfunction associated with pathological conditions or following cardiac-related surgical procedures, these time-dependent mechanical relationships are often altered. This alteration, when combined with the effects of weakened cardiac muscles, reduces the ability of the ventricle to generate contractile strength resulting in hemodynamic insufficiency.

Ventricular dyssynchrony following coronary artery bypass graft (CABG) surgery is a problem encountered relatively often, requiring post-operative temporary pacing. Atrio-biventricular pacing has been found to improve post-operative hemodynamics following such procedures. See Weisse et al., Thorac. Cardiovasc. Surg. 2002;41:131-135. A widely accepted, standardized method for selecting pacing sites and pacing intervals that provide the greatest hemodynamic benefit to the patient during the critical recovery phase, however, has not been available.

Chronic ventricular resynchronization therapy has been clinically demonstrated to improve indices of cardiac function in patients suffering from congestive heart failure. Cardiac pacing may be applied to one or both ventricles or multiple heart chambers, including one or both atria, to improve cardiac chamber coordination, which in turn is thought to improve stroke volume and pumping efficiency. Clinical follow-up of patients undergoing resynchronization therapy has shown improvements in hemodynamic measures of cardiac function, left ventricular volumes, and wall motion. See, for example, Gras D et al., Eur J Heart Fail. 2002;4:311-20; and Sogaard P et al., J Am Coll Cardiol. 2002;40:723-30. However, not all patients respond favorably to cardiac resynchronization therapy. Physicians are challenged in selecting patients that will benefit and in selecting the optimal pacing intervals between the atria and ventricles (A-V intervals) and between the ventricles (V-V intervals), collectively referred to herein as "A-V-V" intervals, applied to resynchronize the heart chamber contractions.

Selection of pacing intervals may be based on echocardiographic studies performed to determine the settings resulting in the best hemodynamic response. Significant hemodynamic changes may not always be acutely observable in an individual patient using non-invasive monitoring methods. Selection of parameters may therefore be based on avoidance of altered or impeded ventricular filling. In the MIRACLE clinical trial conducted to evaluate resynchronization therapy, the A-V-V intervals were optimized individually in patients by shortening the A-V interval to maximize LV filling without truncating the atrial contribution as observed by echocardiography and to maximize stroke volume. Acute increases in stroke volume have been related to chronically sustained clinical benefits. In fact, patients acutely optimized based on stroke volume have exhibited chronic improvements in sustained stroke volume measures.

Echocardiographic approaches for optimizing resynchronization therapy provide only an open-loop method for selecting pacing intervals. After evaluating the hemodynamic effect of varying combinations of pacing intervals, a clinician must manually select and program the desired parameters. Furthermore, an echocardiographic procedure for optimizing resynchronization therapy can require substantial time and personnel. A technician is required to program A-V-V timing schemes while a sonographer interprets the effects on the heart. A period of hemodynamic stabilization is generally desired prior to evaluating the hemodynamic effects of a particular timing scheme. However, the time required to reach hemodynamic stability may be uncertain.

A closed-loop method for selecting pacing intervals for resynchronization therapy that reduces the time and personnel required for testing various A-V-V timing schemes is therefore desirable. A closed-loop method preferably accounts for a period of hemodynamic stabilization and optimizes the A-V-V intervals such that the resultant effect on stroke volume is maximized. Furthermore, a closed-loop method that may be fully implemented in an implantable device would advantageously allow periodic re-optimization of A-V-V intervals in order to maintain an optimal hemodynamic benefit chronically.

Numerous algorithms for optimizing the A-V interval during dual chamber pacing to improve cardiac function or hemodynamic status have been described including automatic algorithms based on an implantable sensor of hemodynamic function. Measurements of impedance to assess cardiac output, intracardiac blood pressure sensors, acoustical sensors for monitoring heart sounds, a Doppler ultrasound sensor for monitoring flow have all been proposed for assessing cardiac function using an implantable device. Reference is made, for example, to U.S. Pat. No. 5,334,222 to Salo et al., and U.S. Pat. No. 6,477,406 issued to Turcott.

Multichamber pacing systems having automated selection of pacing intervals have also been proposed. A four-chamber pacing system that includes impedance sensing for determining the timing of right heart valve closure or right ventricular contraction and adjusting the timing of delivery of left ventricular pace pulses is generally disclosed in U.S. Pat. No. 6223,082 issued to Bakels, et al., incorporated herein by reference in its entirety. Programmable coupling intervals selected so as to provide optimal hemodynamic benefit to the patient in an implantable multichamber cardiac stimulation device are generally disclosed in U.S. Pat. No. 6,473,645 issued to Levine, incorporated herein by reference in its entirety. Improvement in cardiac function is based on a generic physiological sensor. Such automated systems have not been put to clinical use to date.

A need remains, therefore, for a practical method for automatically assessing the hemodynamic response to different A-V-V timing schemes during cardiac resynchronization therapy and identifying optimal A-V-V timing schemes, both acutely and chronically.

SUMMARY OF THE INVENTION

The present invention is directed toward providing a closed-loop method for determining optimal cardiac resynchronization pacing intervals based on a surrogate measurement for stroke volume. The present invention is realized in a cardiac resynchronization system that includes an implantable multi-chamber pulse generator and associated lead system for sensing and pacing in two, three, or all four heart chambers. The system further includes a pressure sensor positioned for the detection of arterial blood pressure, or an alternative sensor for detecting a signal directly correlated to arterial blood pressure. Arterial pressure signal processing is performed to derive one or more signal characteristics as a surrogate for stroke volume. Characteristics include, but are not limited to, maximum pulse pressure, maximum dP/dt, mean pressure, and/or a time interval corresponding to systolic ejection time. For the purposes of the present invention, arterial pressure or pressure correlate is measured after the aortic valve, either in the aorta, or along an arterial branch such as the radial artery.

The present invention provides a method for acutely optimizing cardiac resynchronization pacing intervals based on a stroke volume surrogate derived from the arterial pressure signal or correlate thereof. In this embodiment, arterial pressure may be measured invasively by cannulating an artery, such as the radial artery, and placing a temporary pressure catheter. Non-invasive methods for reliably estimating arterial pressure, for example using a tonometer, phonocardiogram, or other methods, may be substituted for invasive pressure measurement methods. An automated iterative optimization procedure is executed by an external device or "programmer" in telemetric communication with the implanted multi-chamber pacemaker. The external device receives, processes and stores the arterial pressure data via a sensor interface. One or more stroke volume surrogates are determined and stored for each of a set of A-V-V timing schemes. The A-V-V timing scheme producing the greatest stroke volume as determined by the surrogate measurement (s) is automatically programmed as the operating A-V-V intervals for chronic resynchronization therapy.

The present invention further provides a method for chronically maintaining optimal pacing intervals. In this embodiment, an implantable sensor is placed for monitoring aortic or arterial pressure, which sensor may be a pressure sensor placed intra-arterially for direct pressure measurement or a sensor placed extravascularly for measurement of an arterial pressure correlate such as arterial wall distension or flow. The implanted multi-chamber pacemaker performs an automated iterative optimization procedure during which the arterial pressure signal or pressure correlate is processed to determine a stroke volume surrogate during a number of different A-V-V timing schemes. The A-V-V timing scheme producing maximum stroke volume based on the surrogate measurement(s) is automatically programmed as the operating A-V-V intervals. The automated optimization procedure is repeated on a periodic or triggered basis such that the operating A-V-V intervals are periodically updated as necessary to maintain maximal hemodynamic benefit.

The present invention thus provides a method and apparatus for performing acute cardiac resynchronization pacing interval optimization in a reduced time with fewer personnel required. The present invention further provides a method and apparatus for maintaining optimal A-V-V interval settings chronically by maximizing stroke volume. The methods disclosed herein are expected to improve patient benefit from cardiac resynchronization therapy by ensuring the greatest hemodynamic response acutely and chronically.

DETAILED DESCRIPTION OF THE INVENTION

As indicated above, the present invention provides a method for optimizing cardiac resynchronization therapy (CRT). Optimal CRT pacing intervals, which can include a right and/or left atrial-ventricular (A-V) interval and an interventricular (V-V) interval, collectively referred to herein as "A-V-V intervals", are selected based on a surrogate measure of stroke volume. Methods included in the present invention may be implemented in an external device or "programmer" that is in telemetric communication with an implanted multi-chamber pacemaker for acute optimization procedures performed in association with an external pressure measurement device. Methods included in the present invention may additionally or alternatively be implemented in the implantable multi-chamber pacemaker for chronic optimization procedures performed in association with an implantable sensor of aortic or arterial pressure or a correlate thereof.

Figure 1:
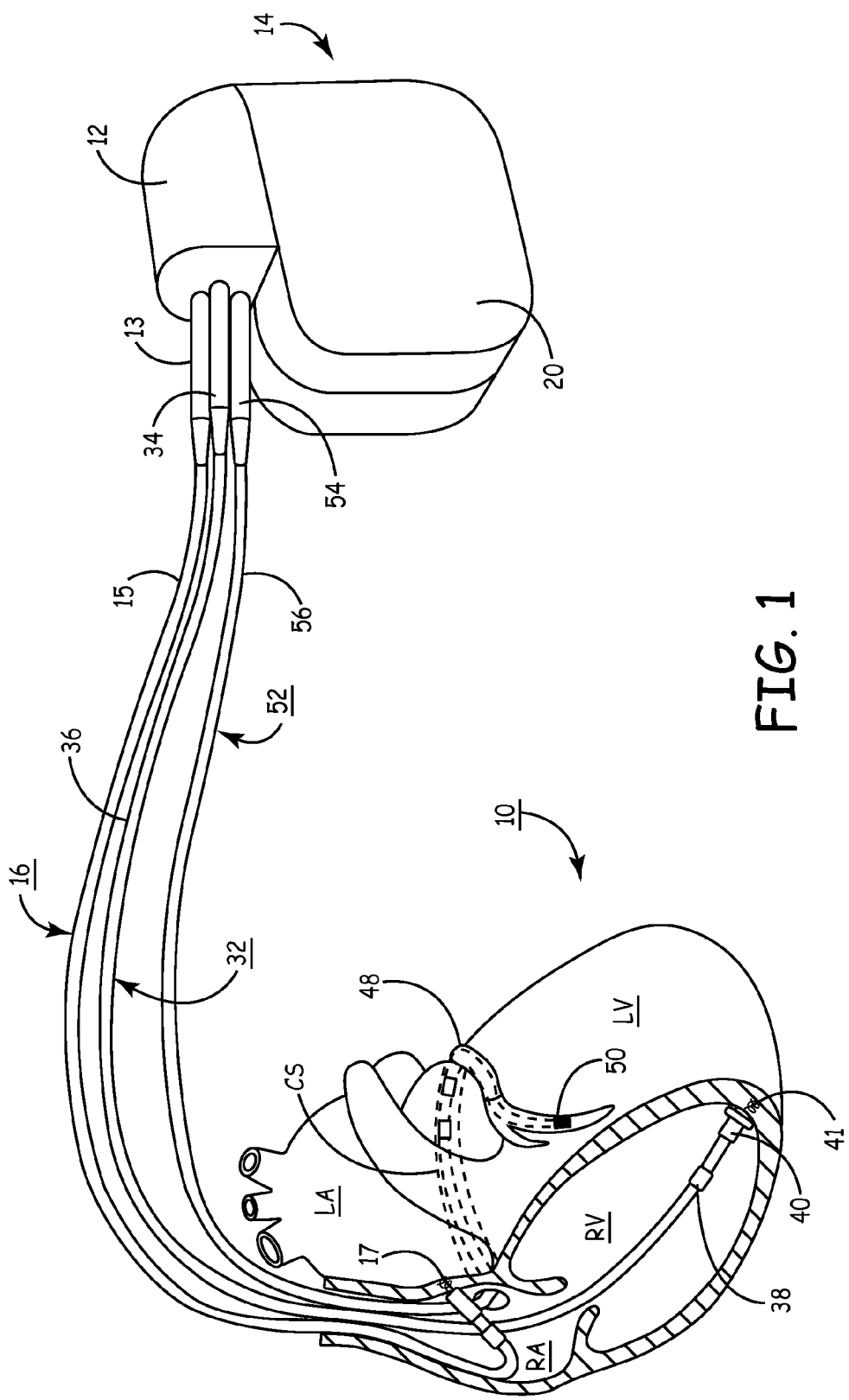
FIG. 1 depicts an implantable, multi-chamber cardiac pacemaker in communication with a patient's heart by way of three leads.

FIG. 1 depicts an implantable, multi-chamber cardiac pacemaker 14 in communication with a patient's heart 10 by way of three leads 16, 32 and 52. The heart 10 is shown in a partially cut-away view illustrating the upper heart chambers, the right atrium (RA) and left atrium (LA), and the lower heart chambers, the right ventricle (RV) and left ventricle (LV), and the coronary sinus (CS) extending from the opening in the right atrium laterally around the atria to form the great cardiac vein 48, which branches to form inferior cardiac veins. The pacemaker 14, also referred to herein as the "implantable pulse generator" or "IPG," is implanted subcutaneously in a patient's body between the skin and the ribs. Three endocardial leads 16, 32 and 52 connect the IPG 14 with the RA, the RV and the LV, respectively. Each lead has at least one electrical conductor and pace/sense electrode. A remote indifferent can electrode 20 is formed as part of the outer surface of the housing of the IPG 14. The pace/sense electrodes and the remote indifferent can electrode 20 can be selectively employed to provide a number of unipolar and bipolar pace/sense electrode combinations for pacing and sensing functions. The depicted positions of leads 16, 32 and 52 and associated electrodes in or about the right and left heart chambers are merely exemplary. Moreover other leads and pace/sense electrodes that are adapted to be placed at electrode sites on or in or relative to the RA, LA, RV and LV may be used instead of the depicted leads and pace/sense electrodes.

The depicted bipolar endocardial RA lead 16 is passed through a vein into the RA chamber of the heart 10, and the distal end of the RA lead 16 is attached to the RA wall by an attachment mechanism 17. The bipolar endocardial RA lead 16 is formed with an in-line connector 13 fitting into a bipolar bore of IPG connector block 12 that is coupled to a pair of electrically insulated conductors within lead body 15 and connected with distal tip RA pace/sense electrode 19 and proximal ring RA pace/sense electrode 21 provided for achieving RA pacing and sensing of RA electrogram (EGM) signals.

Bipolar, endocardial RV lead 32 is passed through the RA into the RV where its distal ring and tip RV pace/sense electrodes 38 and 40 are fixed in place in the apex by a conventional distal attachment mechanism 41. The RV lead 32 is formed with an in-line connector 34 fitting into a bipolar bore of IPG connector block 12 that is coupled to a pair of electrically insulated conductors within lead body 36 and connected with distal tip RV pace/sense electrode 40 and proximal ring RV pace/sense electrode 38 provided for RV pacing and sensing of RV EGM signals.

In this illustrated embodiment, a unipolar, endocardial LV CS lead 52 is passed through the RA, into the CS and further into a cardiac vein to extend the distal LV CS pace/sense electrode 50 alongside the LV chamber to achieve LV pacing and sensing of LV EGM signals. The LV CS lead 52 is coupled at the proximal end connector 54 fitting into a bore of IPG connector block 12. A small diameter unipolar lead body 56 is selected in order to lodge the distal LV CS pace/sense electrode 50 deeply in a vein branching from the great vein 48.

In a four chamber embodiment, LV CS lead 52 could bear a proximal LA CS pace/sense electrode positioned along the lead body to lie in the larger diameter coronary sinus adjacent the LA for use in pacing the LA or sensing LA EGM signals. In that case, the lead body 56 would encase an insulated lead conductors extending proximally from the more proximal LA CS pace/sense electrode(s) and terminating in a bipolar connector 54.

Figure 2:
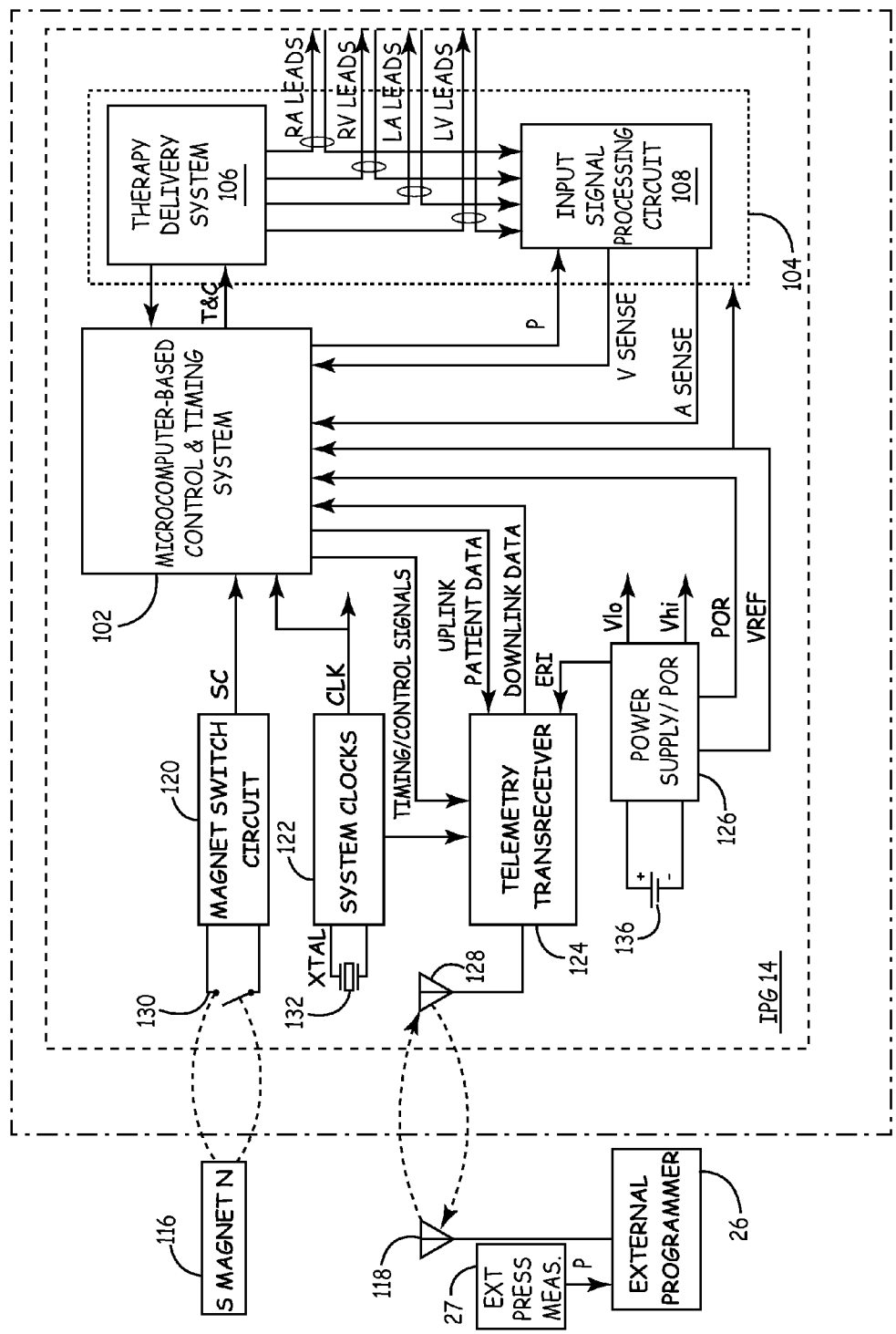
FIG. 2 is a schematic block diagram of the exemplary multi-chamber pacemaker of FIG. 1 that provides delivery of cardiac resynchronization therapy and is capable of processing physiological signal input.

FIG. 2 is a schematic block diagram of the exemplary multi-chamber IPG 14 of FIG. 1 that provides delivery of cardiac resynchronization therapy and is capable of processing physiological signal input. The IPG 14 is preferably a microprocessor-based device. Accordingly, microprocessor-based control and timing system 102, which varies in sophistication and complexity depending upon the type and functional features incorporated therein, controls the functions of IPG 14 by executing firmware and programmed software algorithms stored in associated RAM and ROM. Control and timing system 102 may also include a watchdog circuit, a DMA controller, a block mover/reader, a CRC calculator, and other specific logic circuitry coupled together by on-chip data bus, address bus, power, clock, and control signal lines in paths or trees in a manner known in the art. It will also be understood that control and timing functions of IPG 14 can be accomplished with dedicated circuit hardware or state machine logic rather than a programmed microcomputer.

The IPG 14 includes interface circuitry 104 for receiving signals from sensors and pace/sense electrodes located at specific sites of the patient's heart chambers and delivering cardiac pacing to control the patient's heart rhythm and resynchronize heart chamber activation. The interface circuitry 104 therefore includes a therapy delivery system 106 intended for delivering cardiac pacing impulses under the control of control and timing system 102. Physiologic input signal processing circuit 108 is provided for receiving cardiac electrogram (EGM) signals for determining a patient's heart rhythm. Physiologic input signal processing circuit 108 may additionally receive other physiologic sensor signals, such as a blood pressure signal or correlate thereof as will be further described in conjunction with FIG. 3, and provides physiological signal data to control and timing system 102 for signal processing and analysis. For purposes of illustration of the possible uses of the invention, a set of lead connections are depicted for making electrical connections between the therapy delivery system 106 and the input signal processing circuit 108 and sets of pace/sense electrodes and pressure sensors or other sensors located in operative relation to the RA, LA, RV and LV.

Control and timing system 102 controls the delivery of bi-atrial, bi-ventricular, or multi-chamber cardiac pacing pulses at selected intervals intended to improve heart chamber synchrony. The delivery of pacing pulses by IPG 14 may be provided according to programmable timing intervals, such as programmable conduction delay window times as generally disclosed in U.S. Pat. No. 6,070,101 issued to Struble et al., incorporated herein by reference in its entirety, or programmable coupling intervals as generally disclosed in above-cited U.S. Pat. No. 6,473,645 issued to Levine. Selection of the programmable timing intervals is preferably based on a determination of a stroke volume surrogate as will be described herein. Periodic adjustment of timing intervals may be made automatically or manually based on the determination of the stroke volume surrogate.

The therapy delivery system 106 can optionally be configured to include circuitry for delivering cardioversion/defibrillation therapy in addition to cardiac pacing pulses for controlling a patient's heart rhythm. Accordingly, leads in communication with the patient's heart could additionally include high-voltage cardioversion or defibrillation shock electrodes.

A battery provides a source of electrical energy to power components and circuitry of IPG 14 and provide electrical stimulation energy for delivery electrical impulses to the heart. The typical energy source is a high energy density, low voltage battery 136 coupled with a power supply/POR circuit 126 having power-on-reset (POR) capability. The power supply/POR circuit 126 provides one or more low voltage power Vlo, the POR signal, one or more VREF sources, current sources, an elective replacement indicator (ERI) signal, and, in the case of a cardioversion/defibrillator capabilities, high voltage power Vhi to the therapy delivery system 106. Not all of the conventional interconnections of these voltages and signals are shown in FIG. 2.

Virtually all current electronic multi-chamber monitor/sensor circuitry employ clocked CMOS digital logic ICs that require a clock signal CLK provided by a piezoelectric crystal 132 and system clock 122 coupled thereto as well as discrete components, e.g., inductors, capacitors, transformers, high voltage protection diodes, and the like that are mounted with the ICs to one or more substrate or printed circuit board. In FIG. 2, each CLK signal generated by system clock 122 is routed to all applicable clocked logic via a clock tree. The system clock 122 provides one or more fixed frequency CLK signal that is independent of the battery voltage over an operating battery voltage range for system timing and control functions and in formatting uplink telemetry signal transmissions in the telemetry I/O circuit 124.

The RAM registers included in microprocessor-based control and timing system 102 may be used for storing data compiled from sensed EGM signals and/or relating to device operating history or other sensed physiologic signals for uplink telemetry transmission upon receipt of a retrieval or interrogation instruction via a downlink telemetry transmission. Criteria for triggering data storage can be programmed via downlinked instructions and parameter values. Physiologic data may be stored on a triggered or periodic basis or by detection logic within the physiologic input signal processing circuit 108 upon satisfaction of certain predetermined event detection criteria. In some cases, the IPG 14 includes a magnetic field sensitive switch 130 that closes in response to a magnetic field, and the closure causes a magnetic switch circuit 120 to issue a switch closed (SC) signal to control and timing system 102 which responds in a magnet mode. For example, the patient may be provided with a magnet 116 that can be applied over the subcutaneously implanted IPG 14 to close switch 130 and prompt the control and timing system to deliver a therapy and/or evaluate and/or store physiologic episode data when the patient experiences certain symptoms. In either case, event related data, e.g., the date and time, may be stored along with the stored periodically collected or patient initiated physiologic data for uplink telemetry in a later interrogation session.

Uplink and downlink telemetry capabilities are provided to enable communication with either a remotely located external medical device or a more proximal medical device on or in the patient's body. Stored EGM, or other physiological data as well as real-time generated physiologic data and non-physiologic data can be transmitted by uplink RF telemetry from the IPG 14 to the external programmer or other remote medical device 26 in response to a downlink telemetered interrogation command. As such, an antenna 128 is connected to radio frequency (RF) transceiver circuit 124 for the purposes of uplink/downlink telemetry operations. Telemetering both analog and digital data between antenna 128 and an external device 26, also equipped with an antenna 118, may be accomplished using numerous types of telemetry systems known in the art for use in implantable devices.

The physiologic input signal processing circuit 108 therefore includes at least one electrical signal amplifier circuit for amplifying, processing and in some cases detecting sense events from characteristics of an EGM signal or other physiological sensor output signal. The physiologic input signal processing circuit 108 may thus include a plurality of cardiac signal sense channels for sensing and processing cardiac signals from sense electrodes located in relation to a heart chamber. Each such channel typically includes a sense amplifier circuit for detecting specific cardiac events and an EGM amplifier circuit for providing an EGM signal to the control and timing system 102 for sampling, digitizing and storing or transmitting in an uplink transmission. Atrial and ventricular sense amplifiers include signal processing stages for detecting the occurrence of a P-wave or R-wave, respectively and providing an ASENSE or VSENSE event signal to the control and timing system 102. Timing and control system 102 responds in accordance with its particular operating system to deliver or modify a pacing therapy, if appropriate, or to accumulate data for uplink telemetry transmission in a variety of ways known in the art.

In the embodiment shown in FIG. 2, an external pressure measurement device 27 is shown interfaced with external programmer 26. External pressure measurement device 27 is provided for monitoring a patients arterial pressure during a CRT optimization procedure designed to select A-V-V intervals resulting in the greatest stroke volume. External programmer 26 receives a pressure signal (P) and performs any necessary filtering, amplifying or other signal conditioning and further signal processing of the arterial pressure signal to determine a stroke volume surrogate as will be described in greater detail below. External pressure measurement device 27 is provided as a pressure catheter positioned in a patient's artery, such as the radial artery. Alternatively, external pressure measurement device 27 is provided as a tonometer, or other external, non-invasive device known to provide a signal reliably proportional to arterial pressure.

Figure 3:
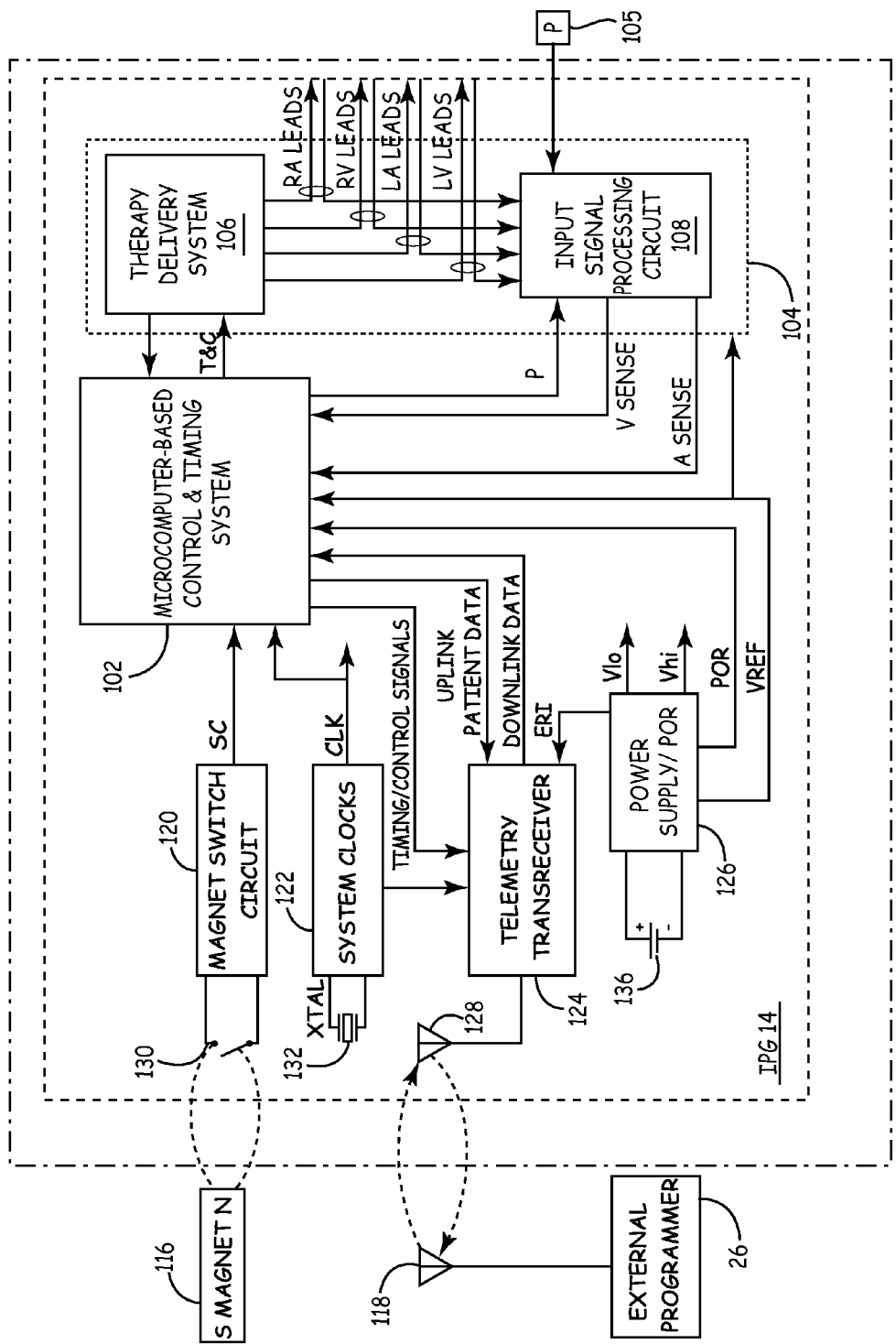
FIG. 3 is a schematic block diagram of an alternative embodiment of multi-chamber pacemaker that includes an implantable sensor for monitoring arterial pressure.

FIG. 3 is a schematic block diagram of an alternative embodiment of multi-chamber IPG 14 that includes an implantable sensor for monitoring arterial pressure. Identically numbered blocks shown in FIG. 3 correspond to those shown in FIG. 2. However, in FIG. 3, input signal processing circuit 108 receives a physiological signal from sensor 105 that is proportional to aortic or arterial pressure. Sensor 105 may be a pressure sensor placed intra-arterially for direct pressure measurement. Sensor 105 may be located on a lead included in the lead system used in conjunction with IPG 14 with the necessary conductors and connectors required to couple sensor 105 to IPG 14. Such a lead may include a sensor of the type disclosed in U.S. Pat. No. 5,564,434 issued to Halperin, et al., incorporated herein by reference in its entirety, which generally discloses a cardiac lead including a capacitive blood pressure sensor. Sensor 105 may alternatively be provided as an extravascular sensor capable of measuring a signal proportional to aortic or arterial blood pressure, such as, but not limited to, an optical, acoustical, piezoelectric, or impedance sensor for measuring arterial wall distension, flow, or other variable proportional to pressure. Examples of extravascular sensors useful for estimating aortic or arterial blood pressure are generally disclosed in the above-cited U.S. Pat. No. 6,477,406 and U.S. Pat. No. 6,491,639 both issued to Turcott, and in U.S. patent application Ser. No. 10/376,063 filed 26 Feb. 2003 and entitled, "METHOD AND APPATATUS FOR CHRONICALLY MONITORING HEART SOUNDS FOR DERIVING ESTIMATED BLOOD PRESSURE" all or which are hereby incorporated by reference herein.

Figure 4:
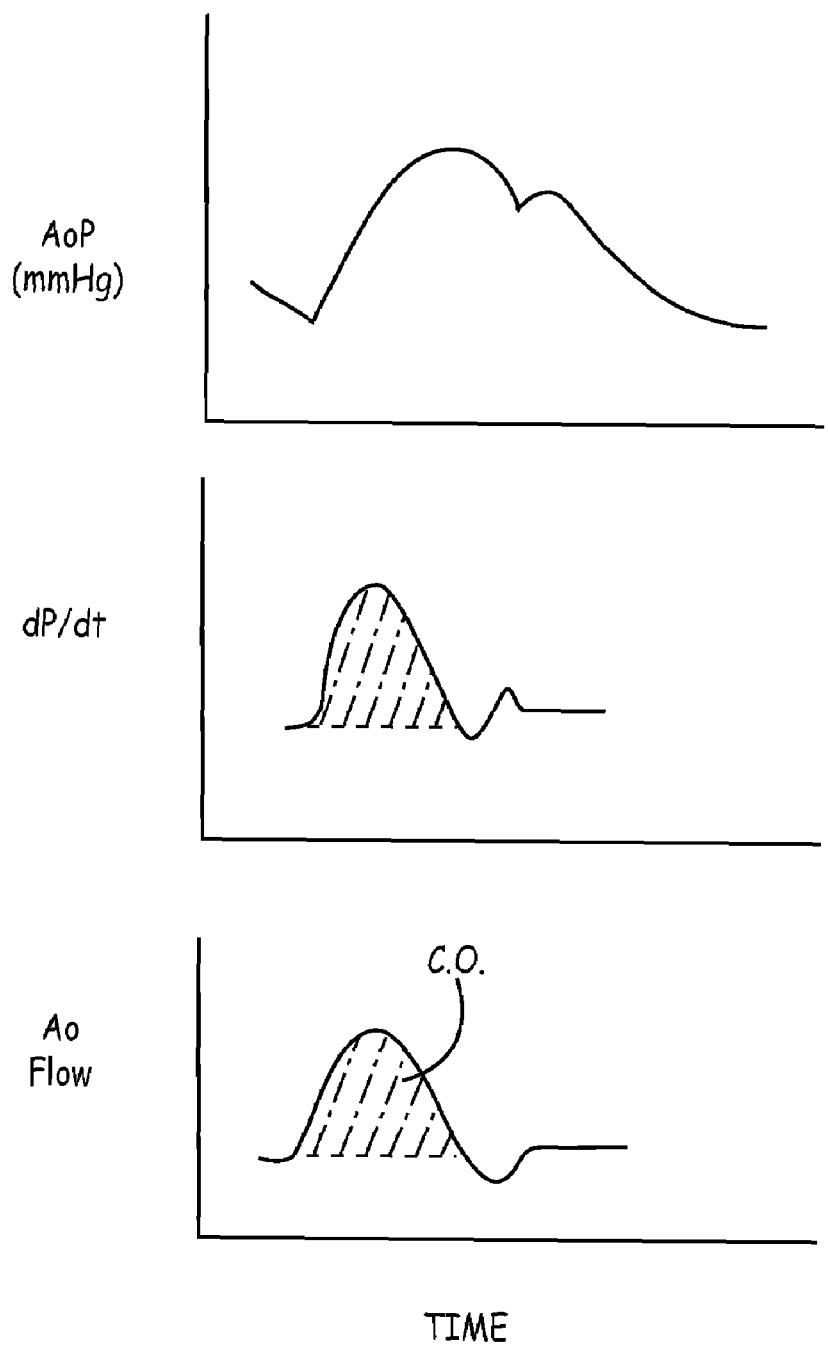
FIG. 4 is a set of graphs showing a representative aortic pressure curve, AoP (top); the first time derivative of aortic pressure, dP/dt, (middle); and aortic flow (bottom) during a single cardiac cycle.

FIG. 4 is a set of graphs showing a representative aortic pressure curve, AoP (top); the first time derivative of aortic pressure, dP/dt, (middle); and aortic flow (bottom) during a single cardiac cycle. The blood volume ejected from the heart during one cardiac cycle, referred to as stroke volume (SV) is equal to the lined area under the aortic flow curve. Aortic flow occurs during the systolic ejection time, which begins upon aortic valve opening and AoP rise and ends upon aortic valve closure at the dichrotic notch of the aortic pressure waveform. Ideally, the total ejection time is increased with proper cardiac synchronization to maximize aortic flow and stroke volume. As can be seen, the dP/dt curve is similar in morphology to the aortic flow curve. Based on this relationship, a stroke volume surrogate can be derived from aortic (or arterial) pressure measurement. Obtaining a pressure signal measured after the aortic valve, in the aorta or a major artery, thus enables a method to be performed for determining a stroke volume surrogate and evaluating the effects of changes in CRT timing schemes on stroke volume.

Figure 5:
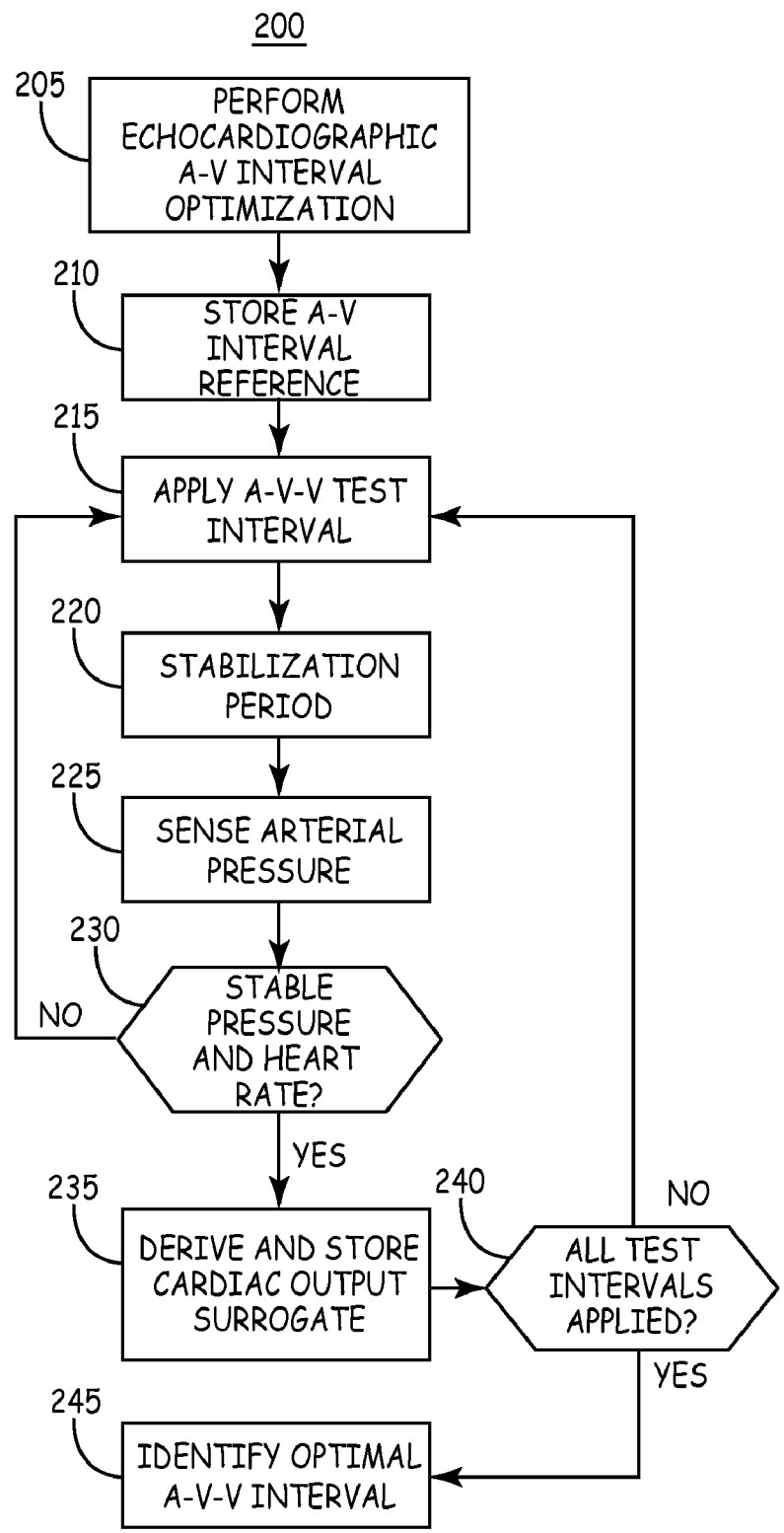
FIG. 5 is a flow chart summarizing the steps included in a method for optimizing cardiac resynchronization therapy.

FIG. 5 is a flow chart summarizing the steps included in a method for optimizing cardiac resynchronization therapy. At step 205, an echocardiographic assessment is performed to identify an optimal A-V interval or A-V interval range that does not result in atrial-ventricular competition. Preferably the shortest A-V interval that does not result in truncation of the atrial contribution to ventricular filling is identified. Shorter A-V intervals can result in overlapping of left atrial and ventricular contraction and abrupt truncation of atrial contraction, resulting in an overall inefficient ejection of blood from the ventricles and mitral valve regurgitation. Longer A-V intervals are undesirable because of fusion between the atrial and ventricular filling phases of the cardiac cycle resulting in altered ventricular filling patterns. This echocardiographic assessment of A-V intervals aimed at optimizing diastolic function provides a reference A-V interval for use during the subsequent A-V-V interval optimization for maximizing systolic function based on the stroke volume surrogate as will be described below.

Alternative methods may be substituted at step 205 for identifying an A-V interval or A-V interval range optimized based on unimpeded diastolic function. In one embodiment, a baseline A-V interval optimization may be performed using right ventricular apical motion.

At step 210, the optimal A-V interval or optimal range identified at step 205 is stored as a reference A-V interval. During the subsequent iterative steps performed to evaluate different A-V-V timing schemes, the test A-V intervals preferably stay within predetermined limits of the reference A-V interval or interval range. In one embodiment, test A-V-V timing schemes incorporate A-V intervals of no more than 20 milliseconds greater or less than the reference A-V interval. This limitation is imposed to avoid truncation of the atrial contribution to ventricular filling, which can be detected by qualitative echocardiographic analysis but may not be detected by other methods.

At step 215, the first of a number of A-V-V timing schemes to be tested is applied. At step 220, an aortic or arterial pressure signal or correlate thereof is sensed. At decision step 230, heart rate and hemodynamic stability are verified. Upon applying a new A-V-V timing scheme, the hemodynamic response may require a period of time before reaching a stable state. A hemodynamic stabilization period may be as short as a few heartbeats or may require several minutes. Preferably, the stabilization period is a variable period of time determined based on hemodynamic monitoring. In one embodiment, a steady state is verified when a running mean value of the sensed pressure signal or pressure correlate does not fluctuate by more than a given percentage, such as 5 to 10%. A running mean pressure value can be determined for a given number of cardiac cycles, such as five cardiac cycles. In an alternative embodiment, the stabilization period is a predetermined, fixed interval of time or number of cardiac cycles.

Heart rate stability is also verified at decision step 230. Heart rate instability, such as the presence of ectopic heart beats, elevated heart rate or other irregularities, would produce anomalous pressure data or pressure data that does not reflect the hemodynamic effect of the applied A-V-V test intervals. As such, the heart rate preferably stays within a specified range. In one embodiment, heart rate stability may be verified by determining the average and standard deviation of the cardiac cycle length during the stabilization period. The cardiac cycle length may be determined as the interval between consecutive atrial or ventricular events including pacing pulses and any sensed atrial or ventricular events. If the average cardiac cycle length or its standard deviation falls outside a predefined range, the data is considered unreliable for A-V-V optimization. Pressure sensing continues at step 220 until hemodynamic and heart rate stability are verified at decision step 230.

Once a steady state is reached, one or more characteristics of the sensed pressure signal or correlate thereof are derived as a stroke volume surrogate at step 235. Derived characteristics can include, but are not limited to, any of: the maximum pulse pressure, maximum positive slope (+$dP/dt_{max}$), mean pressure, and/or a time interval corresponding to the systolic ejection time, such as the interval between a maximum and minimum dP/dt. A derived characteristic is determined for each cardiac cycle and averaged over a predetermined number of cardiac cycles. One or more stroke volume surrogates are determined and stored in device memory with the corresponding A-V-V test intervals.

Method 200 determines at step 240 if all test A-V-V intervals have been applied. If not, method 200 returns to step 215 to apply the next A-V-V test intervals and repeat steps 220 through 235 to determine the hemodynamic effect of the new A-V-V intervals. In one embodiment, A-V-V testing schemes may include V-V intervals of 0, 20, 40 and 80 ms with the 20, 40 and 80 ms intervals each applied such that both right-led ventricular pacing and left-led ventricular pacing are tested. Each V-V interval is applied in conjunction with one or more A-V test intervals. At least an A-V interval equal to the reference A-V interval stored at step 210 is tested in combination with each V-V interval. Additional A-V intervals within a predefined range of the reference A-V interval may be applied in combination with each V-V test interval.

Once all test intervals have been applied, the optimal A-V-V timing scheme is identified at step 245. The optimal A-V-V timing scheme is identified as the interval settings corresponding to the greatest systolic hemodynamic effect as indicated by one or more stroke volume surrogates derived from the arterial or aortic pressure signal or correlate thereof. Operating settings for the A-V-V intervals can then be automatically or manually adjusted to the optimal intervals.

When method 200 is executed by an external device, such as a programmer, for acute CRT optimization, the hemodynamic data and corresponding A-V-V timing schemes can be recorded and displayed with the recommended A-V-V intervals reported. Adjustment of A-V-V intervals may be performed automatically by the external device or manually by an attending clinician.

When method 200 is executed by an implantable device, the hemodynamic data and corresponding A-V-V timing schemes may be stored in device memory for later uplinking to an external device. Method 200 can be performed on a periodic basis such that A-V-V intervals can be automatically adjusted as necessary to maintain the greatest stroke volume. A histogram of automatic adjustments made to the A-V-V intervals may be stored with supporting stroke volume surrogate data so that a history of A-V-V adjustments and hemodynamic data is available to a physician for use in monitoring patient status and therapy effectiveness.

Figure 6:
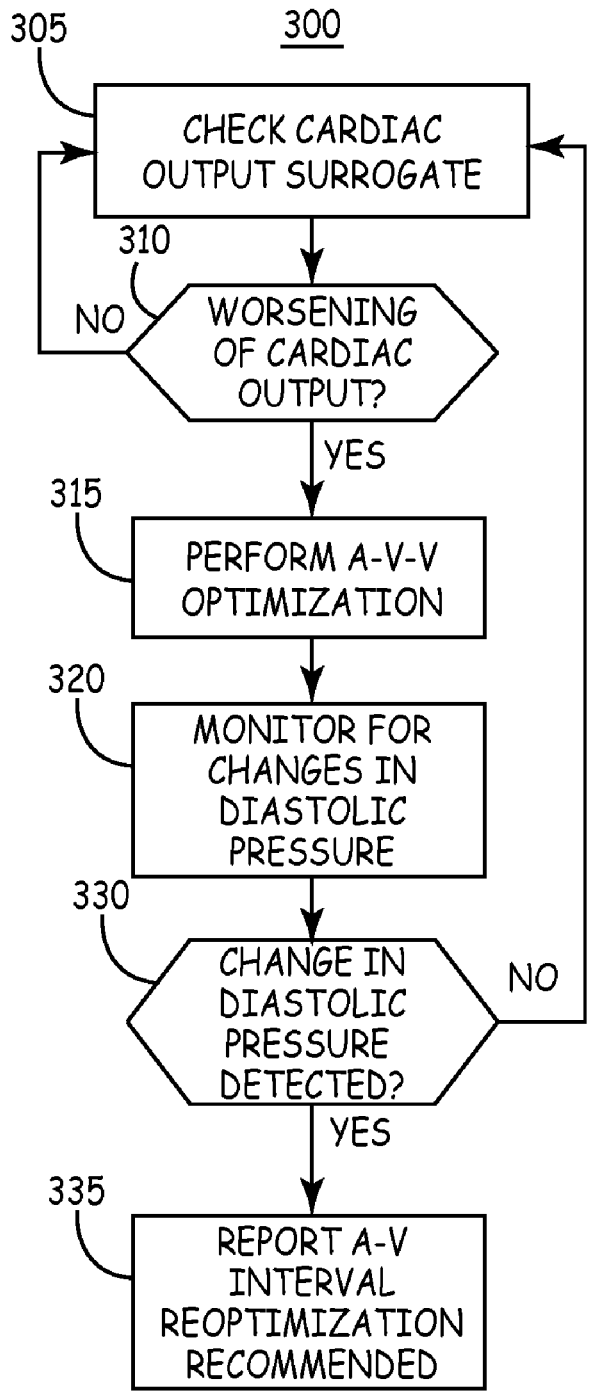
FIG. 6 is a flow chart summarizing a method for maintaining optimal A-V-V intervals chronically.

Method 200 may additionally or alternatively be performed on a triggered basis. Triggering events may be predefined conditions based on sensed physiological signals or a patient-initiated trigger. FIG. 6 is a flow chart summarizing a method for maintaining optimal A-V-V intervals chronically. At step 305, continuous or periodic monitoring of the stroke volume surrogate is performed. The stroke volume surrogate is determined according to the methods described previously based on a sensed aortic or arterial blood pressure signal or correlate thereof. Upon detection of a worsening in stroke volume based on the stroke volume surrogate at decision step 310, the optimization method 200 is performed at step 315 (with the exception of steps 205 and 210) to re-determine the optimal A-V-V timing scheme.

During the re-optimization procedure, changes in diastolic pressure are monitored as indicated by step 320. Mean estimated diastolic pressure or minimum diastolic pressure may be derived from the sensed pressure signal to determine if a change in diastolic pressure has occurred which may be indicative of an alteration of diastolic function. If a change in diastolic function is indicated, the stored A-V interval reference determined at step 205 of method 200 may no longer be valid. A re-optimization of the reference A-V interval based on unimpeded diastolic function may be necessary. At step 335, a warning flag is generated to indicate to a clinician upon the next device interrogation that an A-V interval optimization procedure is recommended.

Thus a method and apparatus have been described for optimizing cardiac resynchronization therapy based on a stroke volume surrogate derived from an arterial or aortic blood pressure signal. While the invention has been described herein in the context of specific embodiments, it is recognized that numerous variations of these embodiments may be apparent to those skilled in the art. The descriptions provided herein, therefore, are intended to be exemplary, not limiting, with regard to the following claims.

The invention claimed is:

1. A method for optimizing cardiac resynchronization therapy comprising:
   a. sensing a signal proportional to a blood pressure development of a patient;
   b. determining a stroke volume surrogate from the sensed signal proportional to blood pressure by deriving a signal characteristic that varies proportionally to stroke volume variations;
   c. at least temporarily storing in a readable storage medium at least a one of the following: the signal, the stroke volume surrogate, the signal characteristic
   d. applying a plurality of A-V-V timing schemes and repeating steps a., b., and c. for at least a subset of said plurality of A-V-V timing schemes; and
   e. identifying an optimal A-V-V timing scheme corresponding to the highest magnitude stroke volume based on the stroke volume surrogate for one of said plurality of A-V-V timing schemes.

2. A method according to claim 1, wherein in the event of degraded diastolic function, performing at least one of the following steps:
   repeating steps a-e and storing a degraded diastolic-function signal.

3. A method according to claim 2, wherein the degraded diastolic function is derived from one of: a relatively decreased mean diastolic pressure and a minimum diastolic pressure.

4. A method according to claim 1, wherein the method is performed manually.

5. A method according to claim 1, wherein the method is performed non-invasively.

6. A method according to claim 1, wherein the method is performed chronically and automatically by operative structure of an implantable medical device (IMD).

7. A method according to claim 6, wherein the IMD comprises one of: a pulse generator, an implantable pulse generator, an implantable cardioverter-defibrillator.

8. A method according to claim 1, wherein the sensed signal proportional to blood pressure comprises a signal provided by one of: a tonometer and a phonocardiogram.

9. A method according to claim 1, wherein the sensed signal proportional to blood pressure comprises a signal provided by one of: an optical sensor, an acoustical sensor, a piezoelectric sensor, an impedance-based sensor.

10. A method according to claim 9, wherein the sensed signal proportional to blood pressure comprises a signal relating to one of: an arterial wall distension metric and a blood flow metric.

11. A method according to claim 1, further comprising conveying at least one of the A-V-V timing scheme and the optimal A-V-V timing scheme to a remote device.

12. A method according to claim 11, wherein the conveying step is performed wirelessly and further comprising:
   performing a mode-switch to a non-rate responsive operational mode during said wireless transmission.

13. A method according to claim 1, wherein the method is performed when an re-optimization signal is manually triggered or stored in a readable memory structure.

14. An apparatus for optimizing cardiac resynchronization therapy comprising:
   a. means for sensing a signal proportional to a blood pressure development of a patient;
   b. means for determining a stroke volume surrogate from the sensed signal proportional to blood pressure by deriving a signal characteristic that varies proportionally to stroke volume variations;
   c. means for, at least temporarily, storing in a readable storage medium at least a one of the following: the signal, the stroke volume surrogate, the signal characteristic
   d. means for applying a plurality of A-V-V timing schemes and repeating steps a., b., and c. for each of said plurality of A-V-V timing schemes; and
   e. means for identifying an optimal A-V-V timing scheme corresponding to the highest magnitude stroke volume based on the stroke volume surrogate for at least one of said plurality of A-V-V timing schemes.

15. An apparatus according to claim 14, further comprising means for repeating steps a-e and storing a degraded diastolic-function signal in the event of a degraded diastolic function.

16. An apparatus according to claim 15, wherein the degraded diastolic function is derived from one of: a relatively decreased mean diastolic pressure and a minimum diastolic pressure.

17. An apparatus according to claim 14 wherein the apparatus comprises one of: a pulse generator, an implantable pulse generator, an implantable cardioverter-defibrillator.

18. An apparatus according to claim 14, wherein the sensed signal proportional to blood pressure comprises a signal provided by one of: a tonometer and a phonocardiogram.

19. An apparatus according to claim 14, wherein the sensed signal proportional to blood pressure comprises a signal provided by one of: an optical sensor, an acoustical sensor, a piezoelectric sensor, an impedance-based sensor.

* * * * *